(12) United States Patent
Desai et al.

(10) Patent No.: US 8,986,291 B2
(45) Date of Patent: Mar. 24, 2015

(54) METHODS AND SYSTEMS FOR CAPTURING AND REMOVING URINARY STONES FROM BODY CAVITIES

(75) Inventors: Rupesh Desai, San Jose, CA (US); Steven Yee, Sunnyvale, CA (US); Robert S. Behl, Palo Alto, CA (US)

(73) Assignee: Percutaneous Systems, Inc., Palo Alto, CA (US)

( * ) Notice: Subject to any disclaimer, the term of this patent is extended or adjusted under 35 U.S.C. 154(b) by 842 days.

(21) Appl. No.: 12/628,382

(22) Filed: Dec. 1, 2009

(65) Prior Publication Data

US 2010/0137846 A1 Jun. 3, 2010

Related U.S. Application Data

(60) Provisional application No. 61/118,802, filed on Dec. 1, 2008, provisional application No. 61/170,055, filed on Apr. 16, 2009.

(51) Int. Cl.
| | |
|---|---|
| *A61B 18/18* | (2006.01) |
| *A61B 19/00* | (2006.01) |
| *A61B 17/221* | (2006.01) |
| *A61B 18/26* | (2006.01) |
| *A61B 1/00* | (2006.01) |
| *A61B 18/24* | (2006.01) |
| *A61B 17/22* | (2006.01) |

(52) U.S. Cl.
CPC .............. *A61B 17/221* (2013.01); *A61B 18/26* (2013.01); *A61B 1/00085* (2013.01); *A61B 18/24* (2013.01); *A61B 2017/22014* (2013.01); *A61B 2017/2215* (2013.01); *A61B 2019/5217* (2013.01)

USPC .................... 606/15; 606/2; 606/13; 128/898

(58) Field of Classification Search
USPC .......................................... 606/2–19; 128/898
See application file for complete search history.

(56) References Cited

U.S. PATENT DOCUMENTS

| | | | |
|---|---|---|---|
| 2,756,752 | A | 7/1956 | Scherlis |
| 3,760,810 | A | 9/1973 | Van Hoorn |
| 3,830,240 | A | 8/1974 | Antonevich et al. |
| 3,870,048 | A | 3/1975 | Yoon |
| 4,030,503 | A | 6/1977 | Clark, III |

(Continued)

FOREIGN PATENT DOCUMENTS

| | | |
|---|---|---|
| DE | 19722429 A1 | 12/1998 |
| DE | 10031661 A1 | 1/2002 |

(Continued)

OTHER PUBLICATIONS

International Search Report and Written Opinion of PCT Application No. PCT/US2009/066281, mailed Jan. 28, 2010, 10 pages total.

(Continued)

*Primary Examiner* — Dawayne A Pinkney
(74) *Attorney, Agent, or Firm* — Wilson Sonsini Goodrich & Rosati (57) ABSTRACT

A stone capture device comprises a shaft with a deployable sweeping structure at its distal end. The shaft is adapted to be removably placed over and connected to a conventional ureteroscope. The combination of the stone capture device and ureteroscope can be introduced into the urinary tract to capture, fragment, and remove stones from the bladder and kidney.

41 Claims, 6 Drawing Sheets

(56) References Cited

U.S. PATENT DOCUMENTS

| | | | |
|---|---|---|---|
| 4,030,505 | A | 6/1977 | Tessler |
| 4,046,149 | A | 9/1977 | Komiya |
| 4,222,308 | A | 9/1980 | Arnett |
| 4,257,420 | A | 3/1981 | Terayama |
| 4,262,677 | A | 4/1981 | Bader |
| 4,295,464 | A | 10/1981 | Shihata |
| 4,471,766 | A | 9/1984 | Terayama |
| 4,486,680 | A | 12/1984 | Bonnet et al. |
| 4,606,330 | A | 8/1986 | Bonnet |
| 4,706,671 | A | 11/1987 | Weinrib |
| 4,735,194 | A | 4/1988 | Stiegmann |
| 4,739,760 | A | 4/1988 | Chin et al. |
| 4,748,971 | A | 6/1988 | Borodulin et al. |
| 4,823,793 | A | 4/1989 | Angulo et al. |
| 4,920,954 | A | 5/1990 | Alliger et al. |
| 5,011,488 | A | 4/1991 | Ginsburg |
| 5,041,093 | A | 8/1991 | Chu et al. |
| 5,135,534 | A | 8/1992 | Tulip |
| 5,154,722 | A | 10/1992 | Filip et al. |
| 5,176,688 | A | 1/1993 | Narayan et al. |
| 5,192,286 | A | 3/1993 | Phan et al. |
| 5,320,627 | A | 6/1994 | Sorensen et al. |
| 5,403,324 | A | 4/1995 | Ciervo et al. |
| 5,423,834 | A | 6/1995 | Ahmed |
| 5,431,676 | A | 7/1995 | Dubrul et al. |
| 5,454,790 | A | 10/1995 | Dubrul |
| 5,476,450 | A | 12/1995 | Ruggio |
| 5,507,797 | A | 4/1996 | Suzuki et al. |
| 5,531,717 | A | 7/1996 | Roberto et al. |
| 5,599,291 | A | 2/1997 | Balbierz et al. |
| 5,676,688 | A | 10/1997 | Jaker et al. |
| 5,711,841 | A | 1/1998 | Jaker |
| 5,716,321 | A | 2/1998 | Kerin et al. |
| 5,814,058 | A | 9/1998 | Carlson et al. |
| 5,836,913 | A | 11/1998 | Orth et al. |
| 5,860,972 | A | 1/1999 | Hoang |
| 5,879,366 | A | 3/1999 | Shaw et al. |
| 5,897,535 | A | 4/1999 | Feliziani et al. |
| 5,906,622 | A | 5/1999 | Lippitt et al. |
| 5,972,019 | A | 10/1999 | Engelson et al. |
| 5,989,264 | A | 11/1999 | Wright |
| 6,007,488 | A | 12/1999 | Jaker et al. |
| 6,039,748 | A | 3/2000 | Savage et al. |
| 6,071,233 | A | 6/2000 | Ishikawa et al. |
| 6,080,174 | A | 6/2000 | Dubrul et al. |
| 6,099,535 | A | 8/2000 | Lamport et al. |
| 6,210,370 | B1 | 4/2001 | Chi-Sing et al. |
| 6,214,037 | B1 | 4/2001 | Mitchell et al. |
| 6,240,968 | B1 | 6/2001 | Bigonzi-Jaker et al. |
| 6,264,664 | B1 | 7/2001 | Avellanet |
| 6,325,812 | B1 | 12/2001 | Dubrul et al. |
| 6,440,061 | B1* | 8/2002 | Wenner et al. ............ 600/114 |
| 6,443,159 | B1 | 9/2002 | Fogarty et al. |
| 6,491,685 | B2 | 12/2002 | Visuri et al. |
| 6,494,893 | B2 | 12/2002 | Dubrul et al. |
| 6,500,182 | B2 | 12/2002 | Foster |
| 6,500,185 | B1 | 12/2002 | Mathews et al. |
| 6,623,508 | B2 | 9/2003 | Shaw et al. |
| 6,645,195 | B1 | 11/2003 | Bhat et al. |
| 6,656,146 | B1 | 12/2003 | Clayman et al. |
| 6,656,191 | B2 | 12/2003 | Ouchi |
| 6,695,834 | B2 | 2/2004 | Gellman et al. |
| 6,749,607 | B2 | 6/2004 | Edwards et al. |
| 6,780,161 | B2 | 8/2004 | Faragalla et al. |
| 6,800,080 | B1 | 10/2004 | Bates |
| 6,869,395 | B2 | 3/2005 | Page et al. |
| 6,929,664 | B2 | 8/2005 | Kolb |
| 6,945,950 | B2 | 9/2005 | Clayman et al. |
| 7,204,804 | B2 | 4/2007 | Zirps et al. |
| 7,214,229 | B2 | 5/2007 | Mitchell et al. |
| 7,217,250 | B2 | 5/2007 | Kolb |
| 7,223,230 | B2 | 5/2007 | Zirps et al. |
| 7,316,663 | B2 | 1/2008 | Whitmore, III |
| 7,462,183 | B2 | 12/2008 | Behl et al. |
| 7,682,366 | B2 | 3/2010 | Sakurai et al. |
| 8,252,017 | B2* | 8/2012 | Paul et al. ............ 606/200 |
| 8,545,526 | B2* | 10/2013 | Martin et al. ............ 606/159 |
| 2001/0044595 | A1 | 11/2001 | Reydel et al. |
| 2002/0068943 | A1 | 6/2002 | Chu et al. |
| 2002/0143326 | A1 | 10/2002 | Foley et al. |
| 2002/0183853 | A1 | 12/2002 | Mitchell et al. |
| 2003/0023247 | A1 | 1/2003 | Lind et al. |
| 2003/0120281 | A1 | 6/2003 | Bates et al. |
| 2003/0144672 | A1 | 7/2003 | Gellman et al. |
| 2003/0176794 | A1 | 9/2003 | Whitman |
| 2004/0092956 | A1 | 5/2004 | Liddicoat et al. |
| 2004/0116941 | A1 | 6/2004 | Reynolds et al. |
| 2004/0122444 | A1 | 6/2004 | Gerard |
| 2004/0127936 | A1 | 7/2004 | Salahieh et al. |
| 2004/0181273 | A1 | 9/2004 | Brasington et al. |
| 2004/0215230 | A1 | 10/2004 | Frazier et al. |
| 2004/0220587 | A1 | 11/2004 | Teague et al. |
| 2005/0033172 | A1 | 2/2005 | Dubrul et al. |
| 2005/0033314 | A1* | 2/2005 | Sakurai et al. ............ 606/127 |
| 2005/0043756 | A1* | 2/2005 | Lavelle et al. ............ 606/200 |
| 2005/0049619 | A1 | 3/2005 | Sepetka et al. |
| 2005/0059981 | A1 | 3/2005 | Poll |
| 2005/0080448 | A1* | 4/2005 | Kear et al. ............ 606/200 |
| 2005/0165412 | A1 | 7/2005 | Secrest et al. |
| 2005/0197627 | A1 | 9/2005 | Huang et al. |
| 2005/0228481 | A1 | 10/2005 | Manasas et al. |
| 2005/0267488 | A1 | 12/2005 | Hare et al. |
| 2005/0277980 | A1 | 12/2005 | Yassinzadeh |
| 2006/0116693 | A1 | 6/2006 | Weisenburgh et al. |
| 2006/0184076 | A1 | 8/2006 | Gill et al. |
| 2007/0016244 | A1 | 1/2007 | Behl et al. |
| 2007/0106233 | A1 | 5/2007 | Huang et al. |
| 2007/0191768 | A1 | 8/2007 | Kolb |
| 2007/0203475 | A1 | 8/2007 | Fischer, Jr. et al. |
| 2008/0058836 | A1 | 3/2008 | Moll et al. |
| 2008/0177277 | A1 | 7/2008 | Huang et al. |
| 2009/0018569 | A1 | 1/2009 | Desai et al. |
| 2009/0287238 | A1 | 11/2009 | Behl et al. |
| 2012/0116443 | A1* | 5/2012 | Ferrera et al. ............ 606/200 |
| 2012/0209282 | A1* | 8/2012 | Teague ............ 606/127 |

FOREIGN PATENT DOCUMENTS

| | | |
|---|---|---|
| EP | 0 605 427 B1 | 12/1992 |
| WO | WO 01/80748 A2 | 11/2001 |
| WO | WO 01/80748 A3 | 1/2002 |
| WO | WO 2005/079678 | 9/2005 |
| WO | WO 2006/060658 A2 | 6/2006 |
| WO | WO 2008/028149 A2 | 3/2008 |

OTHER PUBLICATIONS

US Endoscopy, Foreign Body Management Portfolio [web page]; retrieved from the Internet: <http://www.usendoscopy.com/foreignbody.php>, 3 pages total. [website].

Bard Urological Division Catalog 1990, PA24, "Woven Blasucci Ureteral Catheters", 3 pages.

Garrido et al., "Utilización del catéter "stone sweeper" en la patología litiásica del tracto urinario superior," [The use of Stone Sweeper catheter for stone disease of the upper urinary tract], Arch Esp Urol. Nov. 2006; 56(9):889-892. [English Abstract Only].

L'Esperance et al., "Ureteral Expanding Stent: A New Device for Urolithiasis," J Endourol. May 1, 2007; 21(5): 533-537.

Woitzik et al., "Polyethylene sheath device to reduce tumor cell seeding along the needle tract in percutaneous biopsy," (2003) Surg. Endosc. 17:311-314.

European search report and opinion dated Mar. 30, 2012 for EP Application No. 09830998.2.

European office action dated Nov. 23, 2012 for EP Application No. 09830998.2.

* cited by examiner

METHODS AND SYSTEMS FOR CAPTURING AND REMOVING URINARY STONES FROM BODY CAVITIES

CROSS-REFERENCES TO RELATED APPLICATIONS

The present application claims the benefit of Provisional Application No. 61/118,802, filed on Dec. 1, 2008, and Provisional Application No. 61/170,055, filed on Apr. 16, 2009, the full disclosures of which are incorporated herein by reference.

BACKGROUND OF THE INVENTION

1. Field of the Invention

The present invention relates generally to medical apparatus and methods. More particularly, the present invention relates to a method and apparatus for capturing, fragmenting, and removing urinary stones from the kidney or bladder.

Urinary tract endoscopy, a minimally invasive procedure for removing urinary stones that are present in the bladder, ureter, or kidney, may be performed in several ways. A large viewing scope, referred to as a cystoscope, is advanced from the urethra into the bladder. When necessary, a smaller ureteroscope is further advanced from the bladder, through the ureter, and into the kidney. Alternatively, a nephroscope entering through a percutaneous tract into the kidney, may be used in the kidney and upper urinary tract. In each of these protocols, endoscopes carry either an optical element or optical fiber bundle which in some cases are steerable so that individual stones may be observed, captured, and removed from the kidney and bladder. The endoscopes carry a working channel for the introduction of tools to the distal end of the device. The working channel in a ureteroscope, however, has a very small diameter, due to the very small size of the device itself, typically limiting tool use to one small tool at a time. Optionally, the stones may be fragmented using laser or other energy, and the intact stone and/or fragments may be removed using a deployable basket advanced through a working channel of the endoscope.

Endoscopic stone treatment is particularly difficult to perform in the bladder and kidney where the stones or stone fragments may be mobile and are present in a large open volume and thus are often difficult to capture. While the stones may be captured using a basket or other tools under direct visualization, steering the scope and firmly capturing the stone is problematic, particularly if the stone is mobile and suspended within the open volume. Moreover, if the stone is fragmented with energy, capturing the many stone fragments which disperse throughout the volume and can be even more difficult and time consuming.

For these reasons, it would be desirable to provide improved and alternative apparatus and protocols for the ureteroscopic treatment and removal of stones from the urinary system, particularly the kidney and bladder. Such systems and protocols will preferably be compatible with many or all conventional endoscopes which are commercially available. Desirably, the apparatus and protocols will facilitate capturing of the stones within the open volumes of the kidney and bladder, will allow for energy-based fragmentation of the stones while they remain captured, and will contain most or all of the stone fragments resulting from the fragmentation. The apparatus and protocols would preferably reduce the need to use the working channel of the endoscope, making the working channel available for an energy source or use in new protocols. At least some of these objectives will be met by the inventions described below.

2. Background of the Background Art

Commonly owned, copending application Ser. Nos. 10/886,886; 11/777,515; 12/041,241; and 12/269,739 describe conformable structures which are deployable in the urethra and ureter and which may be used to entrap stones during lithotripsy. Dr. Bogdan Petrut has filed a Romanian Patent Application describing a stone capture device for attaching to a ureteroscope to capture and draw stones into a sheath for containing the stones while delivering laser energy to break up the stones. See also U.S. Pat. Nos. 3,760,810; 3,870,048; 4,222,308; 4,257,420; 4,471,766; 4,735,194; 5,423,834; 5,507,797; 6,099,535; 6,645,195; 6,869,395; 7,204,804; and 7,223,230. U.S. Patent Publication No. US2006/0116693 describes a stone capture device intended for use in lithotripsy treatment. The RothNet® foreign body retrieval device is described at http://www.usendoscopy.com/foreignbody.php.

BRIEF SUMMARY OF THE INVENTION

In a first aspect of the present invention, methods are provided for removing urinary stones from a body cavity, such as a kidney or bladder. The methods comprise introducing a viewing scope, such as a commercially available ureteroscope, having an optical element at its end into an open volume of the body cavity. A perforate sweeping structure is deployed from a distal end of the viewing scope, while the viewing scope is steered and advanced within the open volume of the body cavity to engage the deployed perforate sweeping structure against the stone. Once the stone is engaged, the sweeping structure is further advanced to urge the stone against a wall structure of the body cavity so that the stone is captured between the sweeping structure and the wall structure. Energy is then applied through the viewing scope, typically laser energy delivered via an optical (laser) fiber advanced through a working channel of the viewing scope. The delivered energy disrupts the captured stone and large fragments, producing smaller stone fragments. Usually, the stone is held in place while delivering energy solely by the sweeping structure against the wall structure, and no separate basket, forceps, loop structures, or the like, are used to hold the stone in place. In a preferred aspect of the method, the region around the captured stone is irrigated, typically before, during, and/or after the energy-based fragmentation, to wash the stone fragments into the sweeping structure. Preferred sweeping structures comprise mesh structures, often double-walled mesh structures, in which the stone fragments become entrapped as they are washed away by the irrigating solution.

The viewing scope is usually introduced transluminally, i.e. through the urethra and optionally through the bladder, ureter, and into the kidney. Alternatively, however, the sweeping structure and viewing scope could be introduced through a percutaneous incision in the abdomen.

During delivery and prior to deployment, the perforate sweeping structure is usually maintained in a tubular configuration. Such a tubular structure may be deployed by axial foreshortening. The sweeping structure is disposed over a distal portion of the viewing scope, where the tubular configuration is transformed into a concave structure which extends distally from the distal end of the viewing scope. The concave structure, which may be conical, hemispherical, or have other expansibly tapered structures, will surround the optical element of the viewing scope so that view from the element is not obscured. Moreover, the tubular configuration of the sweeping structure will typically be sufficiently flexible so that the distal end or region of the viewing scope can be steered in a conventional manner without excessive constraint by the sweeping structure. When the tubular configuration of the sweeping structure is shifted to the concave structure, however, it will become more rigid, allowing it to engage, move, and entrap kidney stones against the body cavity wall while retaining sufficient flexibility to conform to an irregularly shaped wall surface. While a preferred perforate sweeping structure is deployed by foreshortening, alternative sweeping structures may have an initial collapsed, closed configuration extending over the distal end of the viewing structure and may be deployed or otherwise opened to a concave configuration surrounding the distal end of the viewing structure, typically by releasing the constrained structure from a surrounding sleeve or other structure.

The methods of the present invention optionally include steering the viewing scope within the body cavity while the distal portion of the viewing scope is present within the tubular configuration of the sweeping structure. Methods further comprise engaging the perforate structure against the urinary stones when said structure is sufficiently rigid to manipulate the stones while remaining sufficiently flexible to conform to an outer rim of the structure to an irregularly shaped bladder wall and sufficiently porous to allow fluids to pass freely through the perforations or apertures in the perforate structure when the region is being irrigated. Generally, the perforate sweeping structure will be formed as a metal or polymeric mesh with individual interwoven wires or filaments. The mesh will have openings or interstices which are sufficiently large to allow the free flow of irrigation fluid, but which have dimensions which contain and/or entrap the stone fragments within the mesh, particularly within a double walled mesh structure which will be described hereinbelow. Usually, porosity of the deployed perforate structure will be sufficient to limit stones larger than 2 mm in any dimension from passing therethrough. The deployed perforate structure utilizes irrigation from the viewing scope to maintain the captured stone fragments (typically smaller than 2 mm) against the interior of the perforate structure and/or against the wall of the body cavity so as not to obscure vision during lithotripsy procedures.

Usually, the perforate sweeping structure will be removably attached to the distal end of the viewing scope. Thus, after the assembly viewing scope and perforate structure has been used in a procedure, the perforate sweeping structure may be detached from the assembly and disposed of while the viewing scope may be sterilized and reused.

While the presently preferred perforate sweeping structure will be an evertable tubular structure, as described above, other embodiments of the perforate sweeping structure include a self-expanding tube or other elongate structure which can be distally advanced from a carrier sleeve or sheath. Usually, the carrier sleeve or sheath will be configured as a "monorail" device which has a relatively short engagement length, typically from 2 cm to 10 cm, usually from 3 cm to 8 cm, with a lumen or passage therethrough which receives the viewing scope. Thus, the carrier sleeve may be advanced over a proximal end of the viewing scope in a manner similar to a monorail vascular catheter. A hypotube or other elongate shaft is attached at the proximal end of the carrier sleeve allowing the carrier sleeve to be pushed over the viewing scope until the sleeve reaches the distal end of the scope. At that point, a second pusher rod or element is used to distally advance a conical (tapered to open in the distal direction) or other expanding mesh structure from the carrier sleeve, where the structure will be configured so that a proximal end is aligned with the optical viewing element of the viewing scope. The assembly of the viewing scope and the carrier sleeve with deployed perforate sweeping structure then can be manipulated and advanced within the open volume of the body cavity to capture stones and engage the stones against a structure, typically a wall of the body lumen, prior to delivering energy to break up the stones. After the stones are broken up, the perforate structure may be proximally retracted so that the structure as well as the stones carried therein are drawn back into the carrier sleeve which may then be withdrawn from the body cavity to remove the stone fragments.

In a second aspect of the present invention, a stone capture device for use with a steerable viewing scope comprises a sheath and a perforate sweeping structure. The sheath has a distal end, a proximal end, and a lumen therebetween, where the lumen is positionable over the distal end of the viewing scope. Usually, the sheath will have a length which extends over most, but not all of the length of the viewing structure, allowing a proximal end of the sheath to be available for manipulation by the treating physician during a procedure. That is, the sheath will have a length sufficient to allow the proximal end of the sheath to lie outside of the patient even when the distal end has been fully advanced into the kidney. Usually, the sheath length will be in the range from 20 cm to 100 cm, more usually from 60 cm to 70 cm when configured for use with a relatively long ureteroscope, and will be in the range from 10 cm to 50 cm, usually from 30 cm to 35 cm when configured to work with a shorter cystoscope or nephroscope.

The perforate sweeping structure will be removably attached to and extend distally from the distal end of the sheath. The perforate sweeping structure will be shiftable between a tubular configuration with a width generally about the same as that of the sheath and a concave configuration which increases in width in the distal direction. A distal end of the viewing scope is disposed within the concave sweeping structure when said sweeping structure is deployed. Prior to deployment, the sweeping structure may be positioned proximally to the distal end of the viewing scope to enhance visibility and/or maneuverability of the distal scope tip. Usually, an optical element of the viewing scope will be generally centered within the deployed sweeping structure. Optionally, the stone capture device may further comprise a means for closing a distal end of the deployed concave sweeping structure to capture the stones therein. Conveniently, the closing means may be a simple wire, suture, or other loop or tether which extends around the distal end of the deployed concave sweeping structure. Thus, the tether can be drawn to close the distal end in the manner of a "purse string." The sweeping structure typically comprises woven or braided filaments which form a mesh tube which can be foreshortened to evert to form a double-walled concave structure. The double-walled concave structure will usually have a conical or hemispherical geometry, typically being advanceable over the viewing scope, typically in a monorail fashion, the position the sweeping structure in the bladder or kidney.

In a preferred configuration where the perforate sweeping structure is attached to the distal end of the viewing scope, the sheath will typically be configured to position the perforate sweeping structure distally over a distal region of the viewing scope while the sweeping structure is in its tubular configuration. By drawing the viewing scope proximally, where the viewing scope is connected to a distal end of the tubular sweeping structure, the tubular configuration of the sweeping structure will be deformed to assume a concave configuration where all or a principal portion of the concave configuration is positioned distally of the distal end of the viewing structure. In its tubular configuration, the sweeping structure will be sufficiently flexible and bendable to allow steering of the viewing structure within the sweeping structure prior to deployment. After deployment into its concave configuration, however, the sweeping structure will assume its double-walled configuration and will have sufficient stiffness to engage and manipulate stones within the body cavity so that the stones may be urged against a cavity wall. Typically, the sweeping structure in its concave configuration will have a bending stiffness which is at least 25% greater than that in the tubular configuration, usually being at least 50% greater, and often being 100% greater or more. The sweeping structure in its concave configuration will further have a width which is greater than that of the sheath, typically being at least twice that of the sheath, often up to eight-fold larger that the sheath width.

The stone capture device is typically packaged as a kit where the sheath and perforate sweeping structure are attached to each other, sterilized, and present in a sterile package, such as a bag, tube, or box. The stone capture device is thus ready to be removably attached to the distal end of a conventional or commercially available viewing scope, such as a ureteroscope, where a distal portion of the scope is placed within the perforate sweeping structure of the capture device. The distal end of the scope will typically be secured to the distal tip of the tubular configuration of the perforate sweeping structure so that retraction of the viewing scope relative to the sheath will foreshorten the perforate sweeping structure causing it to assume the concave configuration.

DETAILED DESCRIPTION OF THE INVENTION

Figure 1:
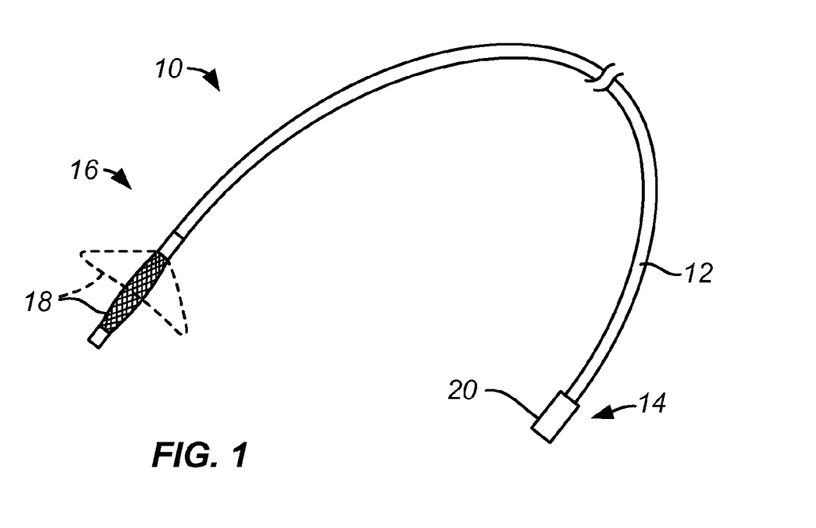
FIG. 1 is a perspective view of a stone capture device constructed in accordance with the principles of the present invention.

Referring to FIG. 1, a stone capture device 10 constructed in accordance with the principles of the present invention comprises a sheath 12 having a proximal end 14 and a distal end 16. A deployable sweeping structure 18 is disposed at the distal end of the sheath 12 and is shiftable between a low profile tubular configuration (shown in full line) and an open or deployed concave configuration (shown in broken line). A hub 20 is typically provided at the proximal end 14 of the sheath 12.

Figure 2:
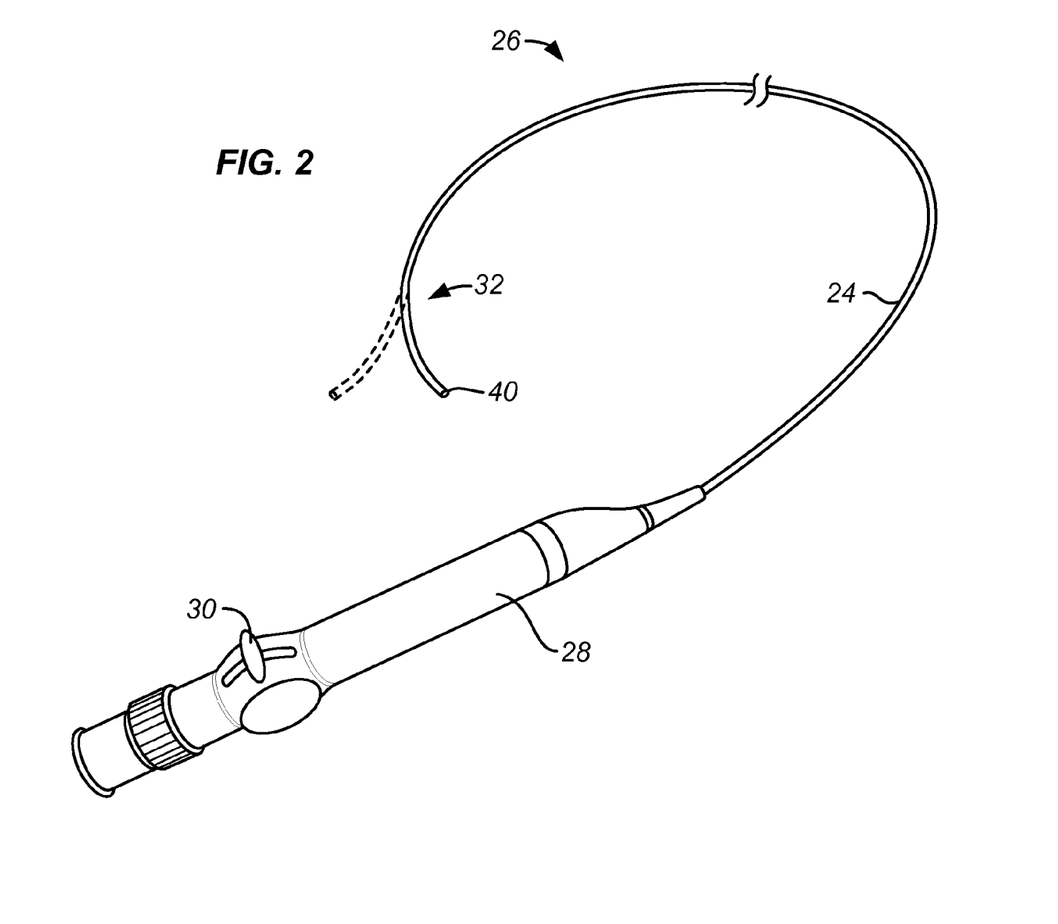
FIG. 2 is a perspective view of a viewing scope in the form of a commercially available ureteroscope having a steerable distal end.

The stone capture device 10 of the present invention is intended to be mounted over the steerable shaft 24 of a conventional viewing scope (26, FIG. 2), typically a uretero-scope, such as those commercially available from Olympus/ACMI. The viewing scope 26 further comprises a control handle 28 attached to a proximal end of the shaft 24. The control handle 28 includes a steering lever 30 which can be advanced and retracted to selectively deflect or "steer" a distal region 32 of the shaft 24, as shown in broken line. The control handle 28 will further include a connector for compiling a light source and an optical element of the viewing scope to a suitable screen and power source (not shown).

Figure 3:
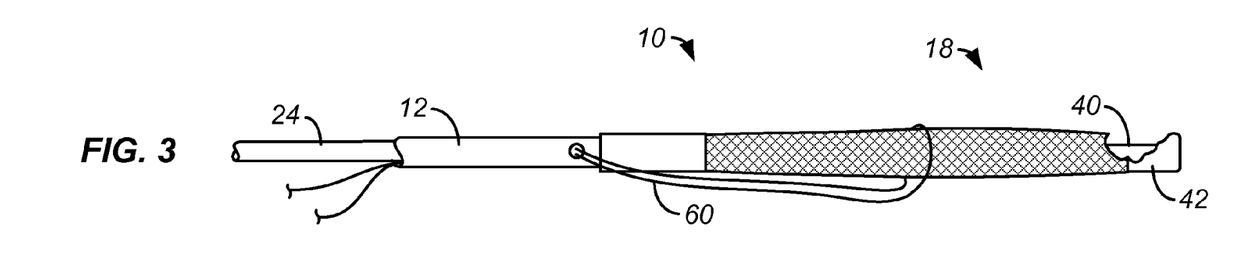
FIG. 3 is a detailed view of the distal end of the stone capture device of the present invention.
Figure 4A:
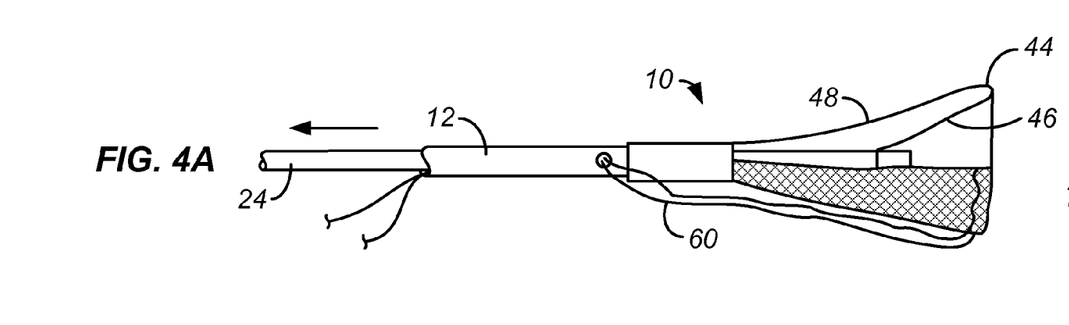
FIGS. 4A and 4B illustrate the distal end of the stone capture device with a partially deployed sweeping structure.
Figure 4B:
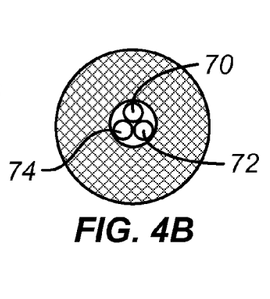
Figure 5A:
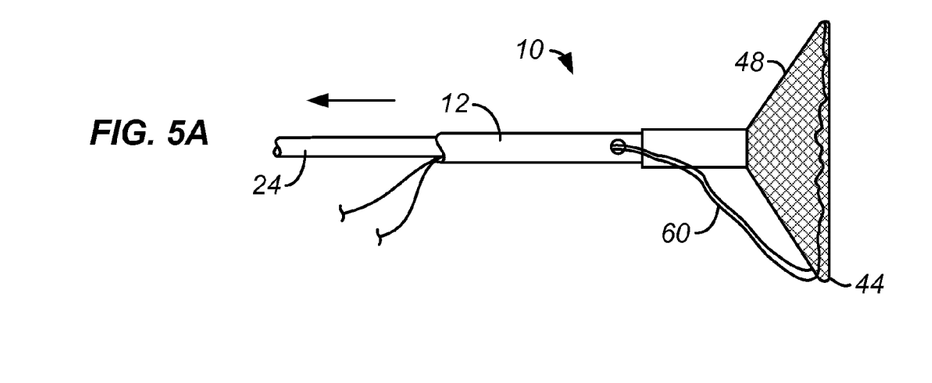
FIGS. 5A and 5B illustrate the distal end of the stone capture device with a fully deployed sweeping structure.
Figure 5B:
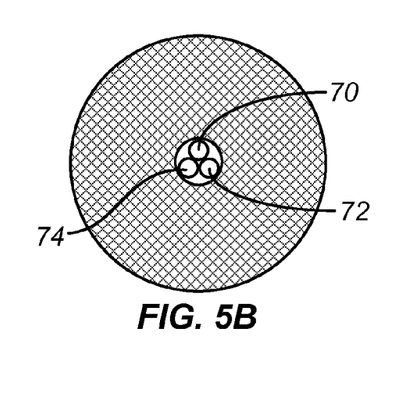

As shown in FIG. 3, a distal tip 40 of the steerable shaft 24 of the viewing scope 26 is introduced through the entire length of the sheath 12 of the stone capture device 10 so that said distal end is received in and attached to a distal tip 42 of the deployable sweeping structure. The deployable sweeping structure 18 is typically a woven or braided mesh, typically formed from polymeric or wire filaments or fibers, so that axial compression of the sweeping structure 18 from its tubular configuration (illustrated in FIG. 3) to a foreshortened configuration (as shown in FIGS. 4A and 5A, will cause the sweeping structure to assume a concave configuration, more particularly a conical configuration. Usually, the sweeping structure will be fabricated so that it preferentially bends and everts about a weakened region 44, as shown in FIGS. 4A and 5A. Thus, a distal most portion 46 of the sweeping structure 18 will preferentially evert into a proximal most portion 48. Thus, as the steerable shaft 24 is progressively pulled proximally, as shown by the arrows in FIGS. 4A and 5A, the steering structure progressively shortens with the forward diameter or width becoming larger.

The sweeping structure in its tubular configuration, as shown in FIG. 3, has only a single wall and is thus relatively flexible, typically having a bending stiffness in the ranges set forth above. As the sweeping structure 18 is everted, however, the wall becomes doubled, increasing the bending stiffness within the ranges set forth above. The relatively flexible tubular configuration is desirable since it will be over the steerable distal region 32 of the viewing scope. Thus, the viewing scope may be steered even while the sweeping structure 18 is over it. When the sweeping structure is deployed, however, it will have more stiffness and rigidity to facilitate engaging and manipulating the urinary stones within the kidney or bladder. As the deployed sweeping structure is distal to the distal end of the steerable shaft 24, however, the structure will not interfere with steering and advancement.

The sweeping structure mesh is preferably constructed from a wire braid. Usually eight to 36 wires are used to construct braid. The wire will usually be formed from a flexible metal or polymer material such as a superelastic nickle-titanium alloy (nitinol), a nylon, or a polyethylene terephthalate (PET).

The sweeping structure 18 will further include a mechanism for drawing the open end closed after it has been partially or fully deployed. In the exemplary embodiments of FIGS. 3, 4A-B, and 5A-B, the structure to close the end is a simple filament or suture 60 which passes through the midsection of the sweeping structure which becomes the forward edge of the sweeping structure after deployment. Thus, by pulling on the filament, the filament acts as a purse string to draw the sweeping structure closed, as illustrated in FIG. 7D discussed below.

Figure 6:
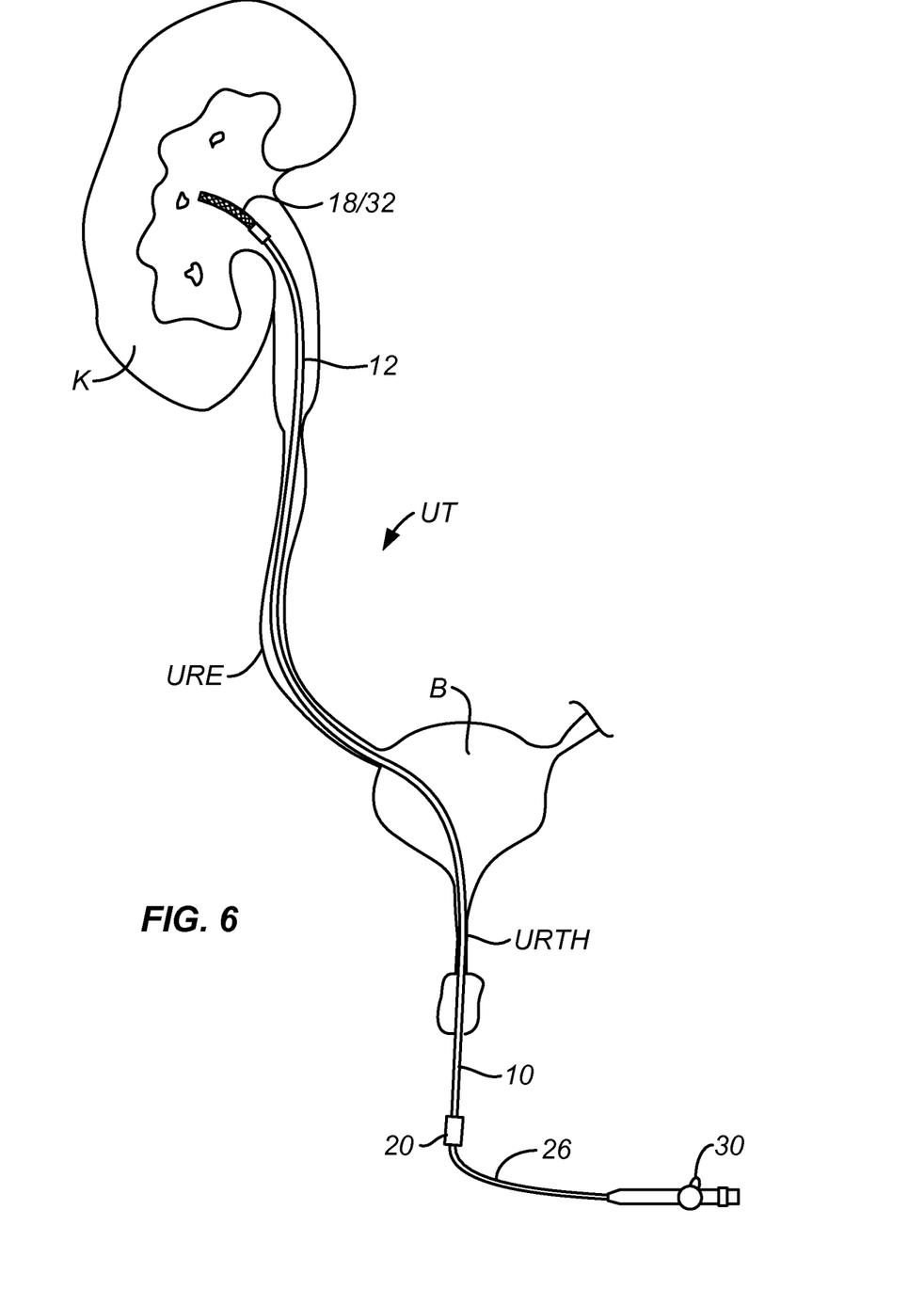
FIG. 6 illustrates the initial placement of the stone capture device and viewing scope of the present invention through the urinary tract into a kidney.

The viewing scope 26 will be introduced into the urinary tract UT with a stone capture device 10 disposed thereover, as illustrated in FIG. 6. The assembly of the viewing scope 26 and the stone capture device 10 is introduced in the same manner as a conventional ureteroscope without the stone capture device. That is, a distal end of the assembly of the present invention will be introduced through the urethra URTH into the bladder B, and optionally further through the ureter URE and into the kidney K. Once in the kidney, the non-deployed sweeping structure 18 and the distal region 32 of the viewing scope may be steered together using the lever 30 of the viewing scope which selectively deflects a distal portion of the shaft 24 of the viewing scope 26.

Figure 7A:
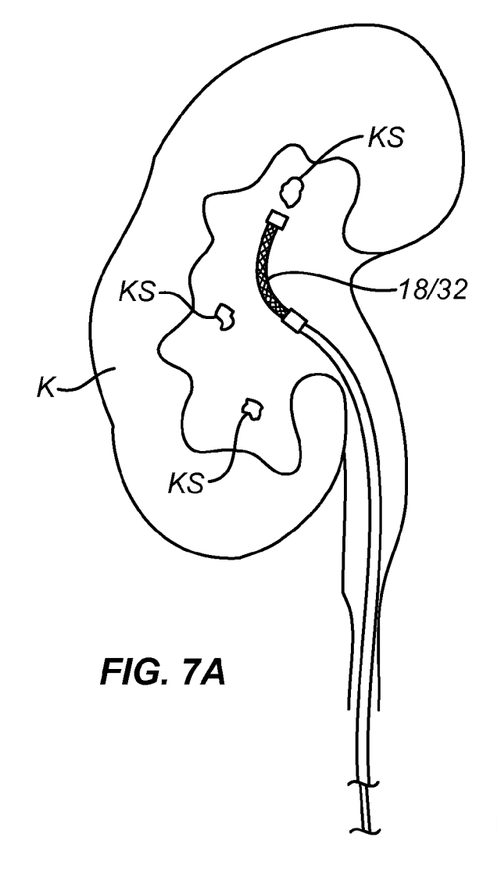
FIGS. 7A-7D illustrate deployment of the sweeping structure on the stone capture device for capturing, fragmenting, and removing a stone within the kidney.
Figure 7B:
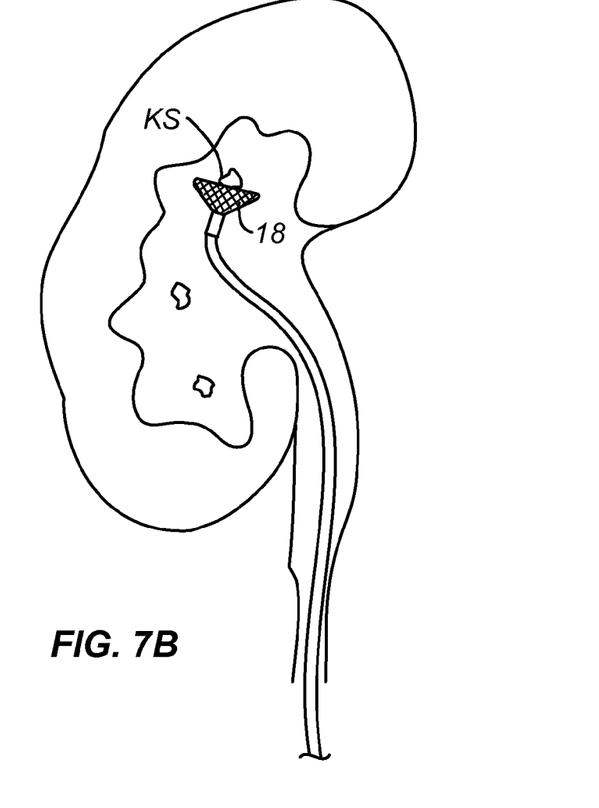
Figure 7C:
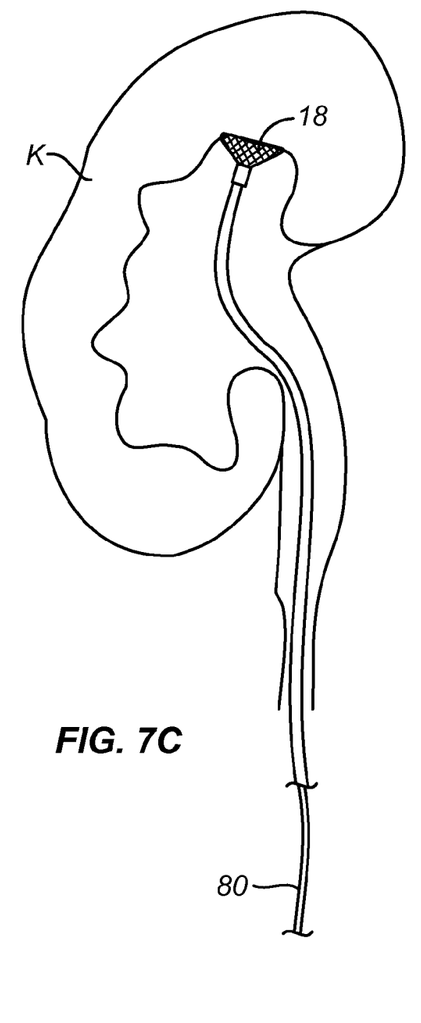
Figure 7D:
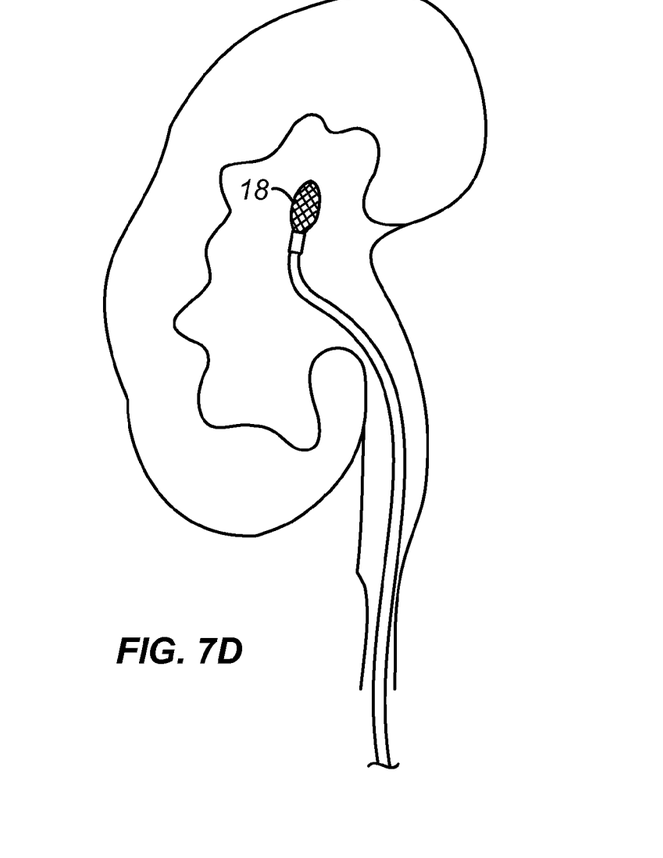

As illustrated in FIG. 7A, the kidney K may have a number of kidney stones KS therein. The sweeping structure 18 and distal region 32 may be steered while the physician views through the optical element 70 of the viewing scope (illustrated in FIGS. 4B and 5B). While viewing, illumination will be provided by a light source 72 on the viewing scope. Once a target kidney stone KS is located, as shown in FIG. 7A, the sweeping structure 18 may be deployed, as shown in FIG. 7B. The combination stone capture device 10 and viewing scope 26 (FIG. 2) may then be advanced, while continuing to optically view the region, until the deployed sweeping structure 18 engages a wall of the kidney, as shown in FIG. 7C, to capture the kidney stone between the sweeping structure and the wall. An optical (laser) fiber 80 or other stone fragmentation device may then be introduced through the working channel 74 (FIGS. 4B and 5B) of the viewing scope and advanced into the region where the stone is captured. By applying laser or other energy to the stone, the stone will be fragmented. Preferably, irrigation medium will be introduced simultaneously through the working channel to sweep the resulting stone fragments into the double-walled mesh of the deployed sweeping structure, thus simultaneously clearing the scope's field of view and entrapping the stone fragments therein. Occasionally, stones in the kidney are trapped within one of the cul-de-sac-like calices of the kidney. The sweeping structure may be advantageously deployed over the mouth of such a calyx to contain the stone and fragments produced by the lithotripsy process, in exactly the same manner as above. After the stone has been fragmented sufficiently, and the stone fragments captured, the filaments 60 may be retracted in order to close the sweeping structure 18 over the stone fragments, as shown in FIG. 7D. At that point, the combined assembly of the stone capture device 10 and the viewing scope 26 may be withdrawn from the urinary tract. After the procedure is complete, the stone capture device 10 may be removed from the viewing scope 26, and the stone capture device will usually be disposed of in a conventional manner. The viewing scope, however, can be sterilized and reused in subsequent procedures.

Figure 8A:
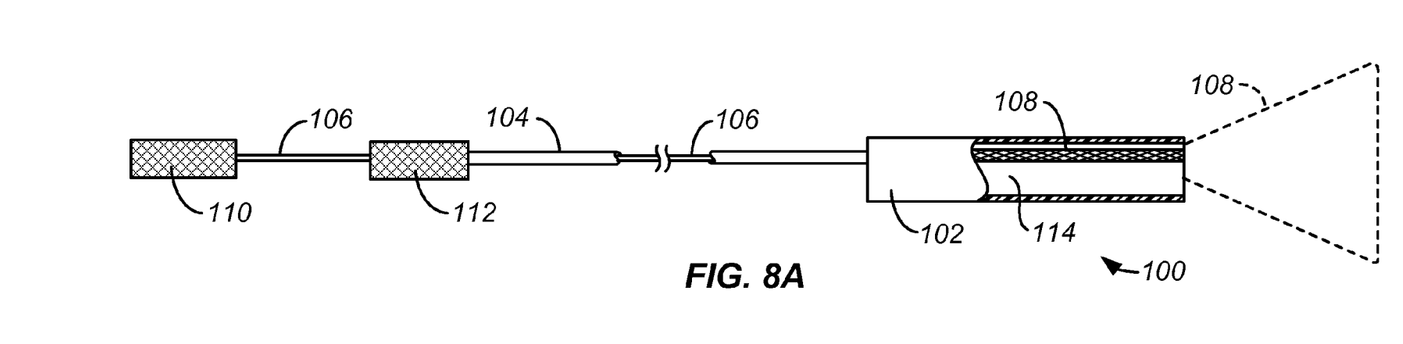
FIGS. 8A-8C illustrate the structure and use of an alternative embodiment of the sweeping structure of the present invention.
Figure 8B:
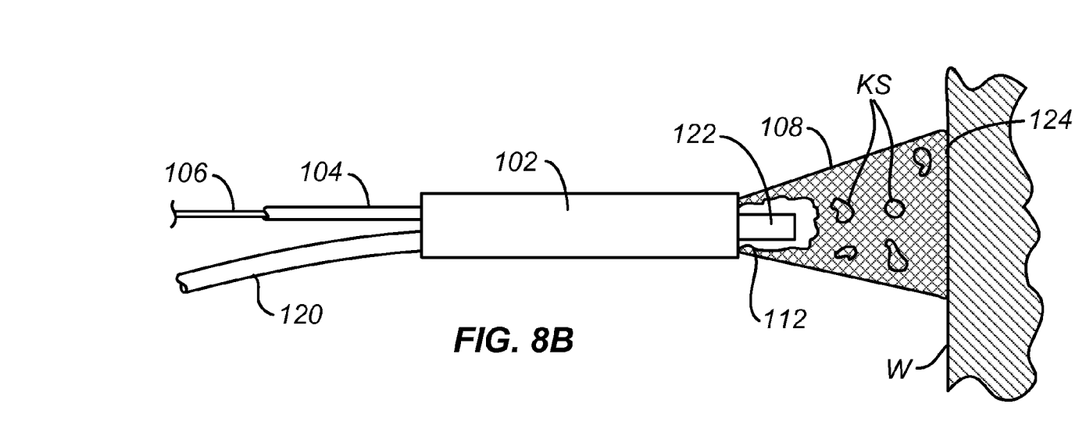

Referring now to FIGS. 8A-8C, an alternative perforate sweeping structure 100 comprises a carrier sleeve 102 attached at the distal end of a hypotube or other elongate tubular member 104. A pusher rod 106 extends coaxially through an inner passage or lumen of the hypotube 104 and is attached to a perforate sweeping structure 108 which is in a proximally retracted, radially collapsed configuration as shown in FIG. 8A. By pushing on the rod 106, typically using handle 110 while holding on to a second handle 112 which is attached at the proximal end of the hypotube 104, the self-expanding perforate sweeping structure 108 can be distally advanced so that it is released from the sleeve 102 and expands into an open conical configuration, as shown in FIG. 8B. A proximal end 112 of the perforate sweeping structure 108 will also expand to open and align with a passage or lumen 114 (FIG. 8A) which runs through the carrier sleeve 102.

Figure 8C:
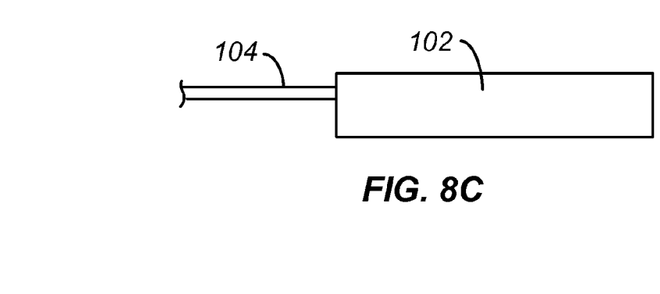

The sweeping structure assembly 100 may then advance over a viewing scope 120 (FIG. 8B) by advancing a proximal end of the scope into the passage 114 of the sleeve 102. The hypotube 104 may be used to distally advance the sleeve 102 over the viewing structure 120 until the sleeve 102 approaches a distal end 122 of the viewing scope 120, as best seen in FIG. 8B. At that point, the viewing scope 120 and/or the assembly of sleeve 102 and hypotube 104 may be manipulated to cause the deployed perforate sweeping structure 108 to capture kidney stones KS therein. By then engaging a distal periphery 124 of the perforate sweeping structure 108 against the wall W, of the body cavity, kidney stones KS may be captured and energy applied through an optical fiber advanced through a working channel of the viewing scope 120 in order to disrupt the stones. After the stones are disrupted into a plurality of small fragments, the hypotube 104 may be retracted proximally in order to draw and collapse the sweeping structure 108 back into the passage 114 of sleeve 102 (as shown in FIG. 8C), optionally after the viewing scope 120 has been at least partially retracted therein. The viewing scope and sweeping structure assembly 100 may then be withdrawn from the body cavity to remove the stones.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for removing a stone from a body cavity selected from the group consisting of a kidney and a bladder, said method comprising:
   mounting a perforate sweeping structure over a distal end of a viewing scope such that the perforate sweeping structure is removably coupled to and encloses the distal end of the viewing scope, the viewing scope having an optical element at the distal end thereof;
   advancing the viewing scope and the perforate sweeping structure in the distal direction into an open volume of the body cavity;
   deploying the perforate sweeping structure from the distal end of the viewing scope, wherein the deployed perforate sweeping structure is in an open concave configuration which increases in width in the distal direction and has an open distal end;
   steering and advancing the viewing scope within the open volume to pass the stone through the open distal end of the deployed perforate sweeping structure, engage the deployed perforate sweeping structure against the stone, and urge the stone and the open distal end of the deployed perforate sweeping structure against a wall of the body cavity to enclose the stone between the deployed perforate sweeping structure and the body cavity wall; and
   applying energy through the viewing scope against the captured stone to break up the stone and produce stone fragments wherein applying energy comprises advancing an energy applying tool through a working channel of the viewing scope, and wherein applying energy comprises delivering mechanical or pneumatic energy.

2. A method as in claim 1, wherein advancing the viewing scope and the perforate sweeping structure into the open volume comprises introducing the viewing scope transluminally into the open volume.

3. A method as in claim 1, wherein advancing the viewing scope and the perforate sweeping structure into the open volume comprises introducing the viewing scope percutaneously into the open volume.

4. A method as in claim 1, wherein deploying the perforate sweeping structure comprises foreshortening a tubular structure disposed over a distal portion of the viewing scope to a concave structure which extends distally from the distal end of the viewing scope and surrounds the optical element, wherein the width of the concave structure is determined by the amount of foreshortening.

5. A method as in claim 4, wherein the concave structure has a generally conical or hemispherical geometry.

6. A method as in claim 1, wherein deploying the perforate sweeping structure comprises opening a collapsed structure extending distally from the distal end of the viewing scope to a concave structure extending distally from the viewing structure and surrounding the optical element.

7. A method as in claim 6, wherein the concave structure has a generally conical or hemispherical geometry.

8. A method as in claim 4, further comprising steering the viewing scope within the body cavity while said distal portion of the viewing scope is within the tubular configuration of the sweeping structure and the sweeping structure is sufficiently flexible to allow such steering.

9. A method as in claim 1, wherein deploying the sweeping structure comprises advancing a carrier sleeve over the viewing scope and advancing a self-opening sweeping structure from the carrier sleeve.

10. A method as in claim 9, further comprising retracting the sweeping structure back into the carrier sleeve after stone fragments have been captured in said sweeping agent.

11. A method as in claim 9, further comprising advancing the carrier sleeve over the viewing scope in as a monorail deployment.

12. A method as in claim 1, wherein the deployed perforate structure is sufficiently rigid to engage and manipulate stones while being sufficiently porous to allow fluids to pass freely.

13. A method as in claim 9, wherein the porosity of the deployed perforate structure will not allow stones or stone fragments larger than 2 mm in any dimension to pass.

14. A method as in claim 1, wherein applying energy comprises delivering light energy and the energy applying tool comprises a laser fiber.

15. A method as in claim 1, wherein applying energy comprises delivering ultrasonic energy and the energy applying tool comprises a sonic transmission column.

16. A method as in claim 1, further comprising viewing the stone using the optical element of the viewing scope while steering and advancing the perforate sweeping structure distally from the viewing scope to engage and capture the stone.

17. A method as in claim 1, further comprising viewing the stone using the optical element of the viewing scope while applying energy through the viewing scope against the captured stone.

18. A method as in claim 1, further comprising irrigating a region around the captured stone to wash the stone fragments into the sweeping structure.

19. A method as in claim 18, wherein the stone fragments are washed into and entrapped by the sweeping structure.

20. A method as in claim 19, wherein the entrapped stone fragments do not obscure the view of the optical element.

21. A method as in claim 19, further comprising closing the sweeping structure over the entrapped stone fragments to secure the fragments within the sweeping structure.

22. A method as in claim 21, further comprising removing the viewing scope and the sweeping structure from the kidney.

23. A method as in claim 22, further comprising removing the sweeping structure from the viewing scope, disposing of the sweeping structure, and reusing the viewing scope.

24. A stone capture device for use with a steerable viewing scope, said device comprising:

a sheath having a distal end, a proximal end, and a lumen positionable over a shaft of the viewing scope to removably couple the sheath to the viewing scope; and a perforate sweeping structure extending distally from the distal end of the sheath and enclosing at least a portion of a distal end of the steerable viewing scope, wherein the perforate sweeping structure is shiftable between a tubular configuration with a width about the same as that of the sheath and an open concave configuration which increases in width in the distal direction and has an open distal end, wherein the distal end of the steerable viewing scope is disposed within the concave sweeping structure when deployed, and wherein the open distal end of the sweeping structure in its concave configuration is configured to be urged against a wall of a body cavity to enclose a stone within the body cavity between the sweeping structure and the cavity wall, the stone passing through the open distal end of the sweeping structure before being enclosed wherein applying energy comprises advancing an energy applying tool through a working channel of the viewing scope, and wherein applying energy comprises delivering mechanical or pneumatic energy.

25. A device as in claim 24, further comprising: means for closing a distal end of the deployed concave sweeping structure to capture stone fragments therein.

26. A device as in claim 25, wherein the means for closing a distal end of the deployed concave structure comprises a tether extending around the distal end of the deployed concave sweeping structure, wherein the tether can be drawn to close the distal end.

27. A device as in claim 26, wherein the sweeping structure comprises woven or braided filaments arranged as a mesh tube which can be foreshortened to evert into a double-walled concave structure.

28. A device as in claim 26, wherein the double-walled concave structure has a generally conical or hemispherical geometry.

29. A device as in claim 24, wherein the sheath is configured to position the perforate sweeping structure distally over a distal region of the viewing scope while the sweeping structure is in the tubular configuration and to position the sweeping structure distally of the viewing scope while the sweeping structure is in its concave configuration.

30. A device as in claim 29, wherein the sweeping structure in its tubular configuration is sufficiently bendable to allow steering of the viewing scope while the distal region is covered by the sweeping structure.

31. A device as in claim 30, wherein the sweeping structure in its concave configuration is sufficiently stiff to engage stones within the body cavity and urge said stones against the cavity wall.

32. A device as in claim 24, wherein the sweeping structure in its concave configuration has a width which is at least twice that of the sheath.

33. A device as in claim 32, wherein the width of the sweeping structure is from twice to eight fold larger than the sheath width.

34. A device as in claim 24, wherein the sheath has a length less than that of the shaft of the associated viewing scope.

35. A device as in claim 24, wherein a distal end of the perforate sweeping structure is removably connectable to a distal end of the steerable viewing scope, wherein a proximal end of the structure can be distally advanced by the sheath to shift the sweeping structure from its tubular configuration to its conical configuration.

36. A device as in claim 24, wherein a proximal end of the sweeping structure is connectable to a distal end of the steerable viewing scope, further comprising means for drawing the distal end of the sweeping structure proximally to shift the sweeping structure from its tubular configuration to its conical configuration.

37. A device as in claim 24, further comprising a package wherein the device is maintained in the sterile package.

38. A system for fragmenting and capturing a stone in a body cavity, said system comprising: a steerable viewing scope adapted for transureteral introduction to the kidney, said scope having a shaft with an optical viewing element at its distal end and a working channel; and a device as in claim 24, wherein the device is receivable over the shaft of the steerable viewing scope.

39. A system as in claim 35, further comprising an optical wave guide advanceable through the working channel and capable of delivering laser energy to ablate a stone captured by the sweeping structure of the stone capture device.

40. A system as in claim 39, further comprises a mechanical tool advanceable through the working channel and capable of mechanically disrupting a stone capture by the sweeping structure of the stone capture device.

41. A stone capture device for use with a steerable viewing scope, said device comprising:
 a sheath having a distal end, a proximal end, and a lumen positionable over a shaft of the viewing scope to removably couple the sheath to the viewing scope; and
 a perforate sweeping structure extending distally from the distal end of the sheath and enclosing at least a portion of a distal end of the steerable viewing scope, wherein the perforate sweeping structure is shiftable between a tubular configuration with a width about the same as that of the sheath and an open a concave configuration which increases in width in the distal direction and has an open distal end, wherein a distal end of the steerable viewing scope attaches to the distal end of the perforate sweeping structure when the steerable viewing scope is disposed within the perforate concave sweeping structure and the sweeping structure is sufficiently flexible and bendable to allow steering of the steerable viewing scope within the sweeping structure prior to deployment to the concave configuration when deployed, and wherein the open distal end of the sweeping structure in its concave configuration is configured to be urged against a wall of a body cavity to enclose a stone within the body cavity between the sweeping structure and the cavity wall, the stone passing through the open distal end of the sweeping structure before being enclosed wherein applying energy comprises advancing an energy applying tool through a working channel of the viewing scope, and wherein applying energy comprises delivering mechanical or pneumatic energy.

* * * * *